(12) United States Patent
Yatcilla et al.

(10) Patent No.: US 11,690,891 B2
(45) Date of Patent: Jul. 4, 2023

(54) **METHODS OF TREATMENT USING DECOLORIZED *ALOE VERA* EXTRACTS**

(71) Applicant: Herbalife International of America, Inc., Los Angeles, CA (US)

(72) Inventors: Michael T. Yatcilla, Los Angeles, CA (US); Troy Smillie, Redondo Beach, CA (US); Joosang Park, Irvine, CA (US); Isabel Andrea Garcia Tornadu, Buenos Aires (AR); Andrea Bertocco, Stanmore (GB); Kan He, Los Angeles, CA (US)

(73) Assignee: Herbalife International of America, Inc., Los Angeles, CA (US)

( * ) Notice: Subject to any disclaimer, the term of this patent is extended or adjusted under 35 U.S.C. 154(b) by 0 days.

(21) Appl. No.: 16/673,845

(22) Filed: Nov. 4, 2019

(65) Prior Publication Data

US 2020/0138895 A1    May 7, 2020

Related U.S. Application Data

(60) Provisional application No. 62/756,449, filed on Nov. 6, 2018.

(51) Int. Cl.
*A61K 36/886* (2006.01)
*A61K 9/00* (2006.01)

(52) U.S. Cl.
CPC .......... *A61K 36/886* (2013.01); *A61K 9/0053* (2013.01)

(58) Field of Classification Search
None
See application file for complete search history.

(56) References Cited

U.S. PATENT DOCUMENTS 5,560,913 A * 10/1996 Kupper .................. A61K 47/36
424/732
2010/0068213 A1    3/2010 Bouritius 2012/0213756 A1    8/2012 Petralia
2015/0023948 A1    1/2015 Mercati
2018/0008661 A1    1/2018 Yatcilla

FOREIGN PATENT DOCUMENTS

WO    WO 09/103093    8/2009

OTHER PUBLICATIONS

Roshan et al., Apr. 2017, Antimicrobial activity of natural products against clostridium difficile in vitro, Journal of Applied Microbiology, 123:92-103.
International Search Report and Written Opinion dated Jan. 21, 2020 in related PCT Application No. PCT/US19/59710.
Atiba et al., Oct. 2015, Aloe vera gel facilitate re-epithelialization of corneal alkali burn in normal and diabetic rats, Clinical Ophthalmology, 9:2019-2026.
Beneke, Jan. 2012, In vitro drug absorption enhancement effects of aloe vera and aloe ferox, Scientica Pharmaceutica, 80(2):475-486.
Chen et al., Aug. 24, 2010, Intestinal drug transport enhancement by Aloe vera, Planta Medica, 76(12):P152.
Haasbroek et al., Jan. 18, 2019, Intestinal drug absorption enhancement by aloe vera gel and whole leaf extract: in vitro investigations into the mechanisms of actions, Pharmaceutics, 11(1):36, 17 pp.
Hussain et al., Nov. 30, 2016, Aloe vera (*Aloe barbarensis* Miller) supplemented probiotic lassi prevents Shigella Infiltration from epithelial barrier into systemic blood flow in mice models, Microbial Pathogenesis, 102:143-147.
Rodriguez et al., Apr. 2010, Aloe vera as a functional ingredient in foods, Critical Reviews in Food Science and Nutrition, 50(4):305-326.

* cited by examiner

*Primary Examiner* — Michael V Meller
(74) *Attorney, Agent, or Firm* — Knobbe Martens Olson & Bear LLP

(57) ABSTRACT

Provided herein is a method for improving the health of an intestinal epithelial barrier using *Aloe vera*. The method may include administering *Aloe vera* extracts to intestinal epithelial cells. The decolorized aloe extract may be whole leaf extract, whole leaf dry extract, inner leaf dry extract, digested whole leaf extract, digested whole leaf dry extract, digested inner leaf dry extract, or a combination thereof.

8 Claims, 3 Drawing Sheets

METHODS OF TREATMENT USING DECOLORIZED *ALOE VERA* EXTRACTS

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 62/756,449, filed Nov. 6, 2018. The aforementioned application is incorporated by reference herein in its entirety, and is hereby expressly made a part of this specification.

BACKGROUND

Field of the Disclosure

*Aloe vera* has been used as a traditional remedy in various preparations that have been administered orally and topically, among other administrative routes. These preparations have been used in many ways, such as to heal wounds, support digestive health, and for cosmetic purposes. Different parts of the leaf have been linked to different health benefits. However, little is known about *Aloe vera*'s bioactivity and mechanism of action.

As a natural ingredient, the composition of *Aloe vera* varies with growing conditions as well as manufacturing process. Traditionally, the whole leaf juice, including the latex, was ingested. The latex served as a laxative to soothe the stomach and to eliminate intestinal parasites. In the market, *Aloe vera* juice is the more commercially relevant product for consumption, with latex constituents such as anthraquinones generally removed via a charcoal filtration process known as decolorization. Limited information is available regarding the biological and physiological effects of *Aloe vera* after the decolorization process.

The present disclosure is directed toward the effects of different decolorized *Aloe vera* extracts on intestinal epithelial barrier health. The present disclosure further discusses the effects of these extracts on barrier function and gene expression.

SUMMARY

In a first aspect, a method for increasing strength of an epithelial cell barrier between the inside of the human gastrointestinal tract and the rest of the body is provided. The method includes administering an effective amount of a composition including decolorized *Aloe vera* extract to the epithelial cell barrier.

In some embodiments, increasing the strength of the epithelial cell barrier comprises an increased transepithelial electrical resistance.

In some embodiments, the extract used in the method for increasing the strength of an epithelial cell barrier is selected from the group including decolorized samples of whole leaf extract (WLC, 5×), whole leaf dry extract (WLD, 100×), inner leaf dry extract (ILD, 200×), digested whole leaf extract (5×dig), digested whole leaf dry extract (100×dig), digested inner leaf dry extract (200×dig), and combinations thereof. In some embodiments, the increased strength is evident four hours after administration of the extract. In some embodiments, the increased strength is evident 24 hours after administration of the extract. In some embodiments, extract is administered at a concentration within the range of about 0.5 mg/ml to about 2 mg/ml. In some embodiments, the extract is administered at a concentration of about 1 mg/ml.

In a second aspect, a method for repairing injury to epithelial cells is provided. The method includes, for example, administering a composition to the epithelial cells, the composition including decolorized *Aloe vera* extract.

In some embodiments, the extract used in the method for repairing injury to epithelial cells is selected from the group including, for example, decolorized samples of whole leaf extract, whole leaf dry extract, inner leaf dry extract, digested whole leaf extract, digested whole leaf dry extract, digested inner leaf dry extract, and combinations thereof. In some embodiments, repair is evident four hours after administration of the extract. In some embodiments, repair is evident 24 hours after administration of the extract. In some embodiments, decolorized inner leaf dry extract is administered at a concentration within the range of about 0.5 mg/ml to about 2 mg/ml. In some embodiments, decolorized inner leaf dry extract is administered at a concentration of about 1 mg/ml.

In a third aspect, a method for repairing injury to an epithelial cell barrier between the inside of the human gastrointestinal tract and the rest of the body is provided. The method includes administering a composition to the epithelial cell barrier, the composition including decolorized *Aloe vera* extract.

In some embodiments, the injury is inflicted by *Clostridium difficile* Toxin A (Tox A). In some embodiments, repairing injury to an epithelial cell barrier comprises increasing transepithelial electrical resistance of the epithelial cell barrier. In some embodiments, repairing the injury to the epithelial cell barrier comprises decreasing permeability of the epithelial cell barrier to FICT-Dextran 4 kDa (FD4).

In some embodiments, the extract used in the method of repairing injury to an epithelial cell barrier between the inside of the human gastrointestinal tract and the rest of the body is selected from the group consisting of decolorized whole leaf extract, whole leaf dry extract, inner leaf dry extract, digested whole leaf extract, digested whole leaf dry extract, digested inner leaf dry extract, or a combination thereof. In some embodiments, the beneficial effect is located in the small intestine. In some embodiments, the beneficial effect is an increase in epithelial barrier strength. In some embodiments, the beneficial effect is repair to injury to an epithelial cell barrier between the inside of the human gastrointestinal tract and the rest of the body. In some embodiments, the repair is evident four hours after administration of the extract. In some embodiments, the repair is evident 24 hours after administration of the extract.

In a fourth aspect, a method of providing a beneficial effect to a gastrointestinal tract of a human is provided. The method includes administering a composition to the human, the composition comprising decolorized *Aloe vera* extract, wherein the extract is selected from the group consisting of: whole leaf extract, whole leaf dry extract, inner leaf dry extract, digested whole leaf extract, digested whole leaf dry extract, digested inner leaf dry extract, or a combination thereof.

In some embodiments, the beneficial effect is located in the small intestine. In some embodiments the beneficial effect is an increase in strength of an epithelial cell barrier between the inside of the gastrointestinal tract and the rest of the body. In some embodiments, the beneficial effect is repair to injury to an epithelial cell barrier between the inside of the gastrointestinal tract and the rest of the body. In some embodiments, the beneficial effect is expression of human growth factor.

In some embodiments, the beneficial effect is evident four hours after administration of the extract. In some embodiments, the beneficial effect is evident 24 hours after administration of the extract. In some embodiments, the beneficial effect is immune modulation by stimulation of macrophages towards both M1 (inflammatory) and M2 (anti-inflammatory) polarization.

BRIEF DESCRIPTION OF THE DRAWINGS

Features of the present disclosure will become more fully apparent from the following description and appended claims, taken in conjunction with the accompanying drawings. It will be understood that these drawings depict only certain embodiments in accordance with the disclosure and, therefore, are not to be considered limiting of its scope; the disclosure will be described with additional specificity and detail through use of the accompanying drawings. An apparatus, system or method according to some of the described embodiments can have several aspects, no single one of which necessarily is solely responsible for the desirable attributes of the apparatus, system or method. After considering this discussion, and particularly after reading the section entitled "Detailed Description of Certain Embodiments" one will understand how illustrated features serve to explain certain principles of the present disclosure.

DETAILED DESCRIPTION OF CERTAIN EMBODIMENTS

Figure 1:
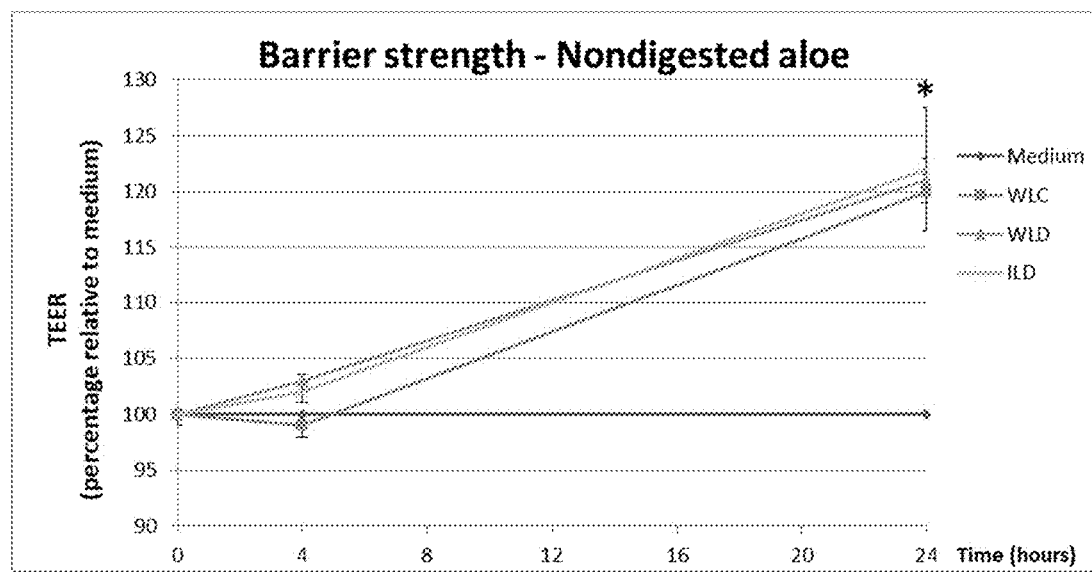
FIG. 1 shows the relative change in epithelial barrier strength as compared with the medium for the three decolorized aloe samples WLC (5×), WLD (100×), and ILD (200×) over time.

A validated in vitro Transwell system employing Caco-2 cell line and macrophages is frequently used to study the strength and integrity of intestinal epithelial barrier, key in maintaining intestinal health by providing a physical barrier, and the gene expression of macrophages, key to maintaining gastrointestinal immune homeostasis through polarization towards tolerant and/or inflammatory phenotypes. Previous research on *Aloe vera* showed that it could contribute to improved health in multiple ways, including wound healing and immune modulation. On the other hand, inclusion of in vitro digestion steps into experimental procedures may be appropriate as it would mimic natural intestinal activity.

Leaky gut is studied nowadays because it is suspected to be involved in some serious health troubles and diseases, such as chronic fatigue syndrome, IBS, metabolic disorders, inflammatory bowel diseases, type 1 diabetes, allergies, asthma, and autoimmune disease. In fact, leaky gut identifies the association between disrupted intestinal barrier function and the development of autoimmune and inflammatory diseases. The epithelium maintains its selective barrier function through the formation of complex protein-protein networks that mechanically link adjacent cells and seal the intercellular space. An improper functioning or regulation of the tight junctions may be responsible for larger intercellular spaces with luminal element passage through the barrier, allowing harmful substances to circulate throughout the body. This can lead to consecutive local and systemic inflammation.

Chronic inflammation is a pathological condition characterized by continued active inflammation response and tissue destruction. Many studies suggest that chronic inflammation could have a serious role in a wide variety of age-related diseases including diabetes, cardiovascular and autoimmune diseases Inflammatory processes induce oxidative stress and reduced cellular antioxidant capacity. Overproduced free radicals react with cell membrane fatty acids and proteins, impairing their function permanently. In addition, free radicals can lead to mutation and DNA damage that can be a predisposing factor for cancer and age-related disorders.

The present disclosure evaluates possible effects of different decolorized *Aloe vera* extracts on intestinal epithelial barrier health. To this end, a human intestinal cell line model featuring Caco-2 cells was used. The results related to barrier function and gene expression were collected and analyzed.

The aloe products disclosed herein include three different *Aloe vera* decolorized extracts: whole leaf extract 5× concentrate (WLC), whole leaf dry extract 100× concentrate (WLD), and inner leaf dry extract 200× concentrate (ILD). Both *Aloe vera* whole leaf extracts (WLC and WLD) are initially processed in the same manner. The *Aloe vera* whole leaf juice is obtained by grinding or macerating the entire *Aloe vera* leaf followed by purification to remove the phenolic compounds found in the latex. This purification step is accomplished via activated carbon filtration in a process known as decolorization. The solvent (water) is then removed until the extracts reach the requisite concentrations of 5× for WLC meaning that 1 kilogram of this material would have been derived from about 5 kilograms of starting whole *Aloe vera* leaf or completely dried to the 100× extract for WLD meaning that 1 kilogram of this material would have been derived from about 100 kilograms of starting whole *Aloe vera* leaf. The *Aloe vera* inner leaf extract 200× (ILD) is obtained by stripping away the outer leaf rind, rinsing or washing away any latex present, and processing the remaining inner leaf material by grinding or macerating the inner *Aloe vera* leaf fillet followed by purification to remove the phenolic compounds found in the latex. This purification step may also be accomplished via decolorization. The extract is then dried down until it reaches total dryness delivering the requisite concentration of 200× meaning that 1 kilogram of this material would have been derived from about 200 kilograms of starting *Aloe vera* inner leaf.

Experiments were also conducted testing digested products of WLC, WLD, and ILD which were processed as in ¶[0027]. Digested products were tested in parallel, to better mimic the in vivo environment. Digested aloe extracts were prepared as follows. Each sample underwent a simulated digestion step by adding 50% by weight 150 mmol/L NaCl+5 mmol/L KCl to each of the aloe samples. The resulting solutions were each mixed with a hand blender and transferred to a 50 mL tube. The pH was adjusted to 2 with HCl, and 0.667 mL of porcine pepsin was added, after which the samples were incubated for 30 min at 37° C. $NaHCO_3$ (1 mol/L) was added to raise pH to at least 5.8, followed by addition of 0.95 mL of porcine pancreatin (4 g/L) and addition of 0.5 mL of a mixture of sodium taurocholate and sodium glycodeoxycholate. The samples were adjusted to a pH of 6.5 with $NaHCO_3$, the headspace was flushed with nitrogen and the sample was subsequently incubated for 1 h at 37° C. The pH of the sample was then adjusted to 7.5 with $NaHCO_3$ and the weight of the sample was adjusted to 30 g. Samples were centrifuged for 30 min at 3023×g at 4° C. The supernatant was removed, and the test tube was flushed with nitrogen and stored at −80° C. until the sample was used.

In some embodiments, the *Aloe vera* composition described herein may be administered to a mammal to improve the health of the intestinal epithelial barrier. In some embodiments, the mammal is a human.

In some embodiments, the *Aloe vera* composition described herein may be administered to a mammal to induce beneficial effects on the intestinal epithelial barrier. Such beneficial effects on the intestinal epithelial barrier include, but are not limited to: an increase in epithelial barrier strength, epithelial permeability, repair to injury of the epithelial barrier, transport of nutrients, and expression of genes related directly or indirectly to intestinal epithelial barrier health.

In some embodiments, the effects of different decolorized *Aloe vera* extracts were tested with a model of the human small intestinal epithelium. For this, Caco-2 cells (American Type Culture Collection) were grown in a transwell system to create apical (luminal) and basolateral (lamina propria) compartments. The cells were subsequently exposed to the different digested and non-digested decolorized *Aloe vera* extracts and the results were monitored.

In some embodiments, the effects of different decolorized *Aloe vera* extracts on the gene expression of immune cells were tested with a model of the human small intestinal epithelium. For this, Caco-2 cells (American Type Culture Collection) were grown in a transwell system to create apical (luminal) and basolateral (lamina propria) compartments while primary macrophage cells were grown, separately from Caco-2 cells, in the bottom reservoir of the system. The Caco-2 cells were subsequently exposed to the different decolorized *Aloe vera* extracts and the gene expression of macrophages as well as Caco-2 cells were analyzed.

EXAMPLES

Statistical Analysis

The differences between the means were analyzed by repeated measured ANOVA, followed by Fisher test. In all cases, $p<0.05$ was considered significant.

Example 1. Epithelial Cell Viability

The viability of Caco-2 cells exposed to the different decolorized *Aloe vera* extracts was determined via trans-epithelial electrical resistance (TEER). TEER is an indication of barrier integrity. Caco-2 cell viability was also determined via MTT (3-[4,5-dimethylthiazol-2-yl]-2,5-diphenyltetrazolium bromide; thiazolyl blue) conversion (Thermofisher), which is a measure of cell metabolic activity.

The effect of three sample concentrations (0.5, 1.0, and 2 mg/mL) of non-digested decolorized products: WLC (5×), WLD (100×), and ILD (200×); and the effect of three sample concentrations (diluted 1:1, 1:2, and 1:3 in medium) of digested products (120 mg of WLC, 144.6 mg of WLD, and 450 mg of ILD) were analyzed after 24 hours of exposure. TEER values of all doses were around 90%, and MTT values were around 100%. Detrimental effects were not observed for any sample. A concentration of 1 mg/mL of non-digested and 1:1 dilution of digested product was determined to be used for subsequent experiments.

Example 2. Effect on Intact Epithelial Barrier

The effects of the different decolorized *Aloe vera* extracts on Caco-2 cell barrier function were analyzed by measuring TEER. First, Caco-2 cells (American Type Culture Collection) were used between passage number 30 and 40 and grown in DMEM medium (Gibco) supplemented with 10% FBS (Hyclone) on transwell inserts in 24-well plates (Greiner Bio-one). The culture was seeded with $3.375 \times 10^4$ Caco-2 cells in 150 μl in the apical department and incubated at 37° C. with 5% $CO_2$ for 21 days to form a monolayer on the apical side of the trans-well semipermeable barrier. To initiate experiments, first basolateral and subsequently apical medium was removed. Next, Caco-2 cells were exposed to apical medium containing either digested (1:1 diluted) or non-digested (1 mg/ml) extracts of decolorized WLC (5×), WLD (100×), and ILD (200×), after which basolateral medium was added.

To measure TEER, 24-well plates with Caco-2 cell monolayer were placed on a hot-plate set to 40° C. TEER measurements were performed by positioning an electrode in the apical compartment and an electrode in the basolateral compartment and measuring the resistance in ohms. The electrodes were washed with medium between measurements of different stimuli. As shown in FIG. 1, no differences were found at 4 hour of treatment between the non-digested extracts. After 24 hours of stimulation all extracts showed an increase in TEER values ($p<0.001$, in all cases).

Figure 2:
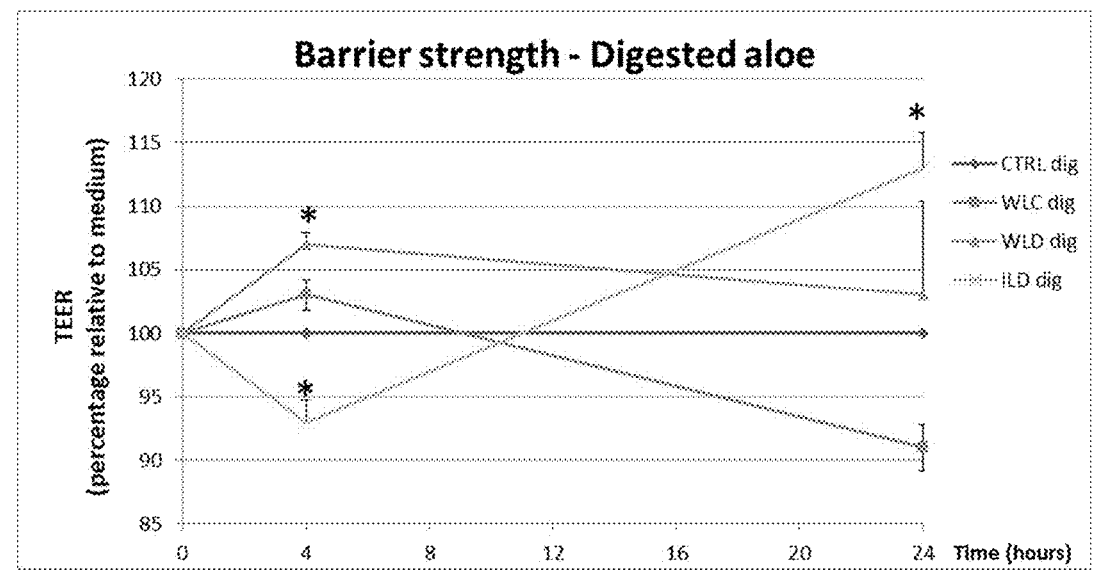
FIG. 2 shows the relative change in epithelial barrier strength as compared with the medium and a digested control sample (CTRLdig) for the three decolorized digested aloe samples WLC (5×dig), WLD (100×dig), and ILD (200×dig).

A similar stimulation was performed with digested products which better mimic the intestinal situation (FIG. 2). The pattern was slightly different compared with non-digested samples. At 4 hours of treatment, TEER increased for 100× (P=0.009) and decreased for 200× (P=0.000007). After 24 hours of treatment only 200× increased TEER values compared with control (P=0.000008).

Example 3. Effect on Challenged Epithelial Barrier (Recovery/Wound Healing)

The reduction in harmful effects to the intestinal epithelium after inflicting damage with *Clostridium difficile* toxin A (Tox A) was measured by TEER and also by translocation (apical to basolateral) of 4 kDa FITC-Dextran (FD4 passage), a fluorescently labeled marker. After monolayer formation as described in [0032], Caco-2 cells were exposed to apical medium containing either digested (1:1 diluted) or non-digested (1 mg/ml in medium) extracts of WLC (5×), WLD (100×), and ILD (200×), mixed with or without 0.25 mg/ml FD4 and/or 0.25 ug/ml ToxA. To detect FD4 passage, 100 μl of basolateral medium was harvested after 4, 8, and 24 hours of Caco-2 stimulation. The medium was transferred to a flat-bottom 96-well black plate and fluorescence was detected by 485 nm excitation and detection of 582 nm emission on a microplate reader (Infinite® 200 PRO, Tecan). To quantify the FD4, a standard curve with two-fold dilutions starting at 500 µg/mL was used.

Figure 3:
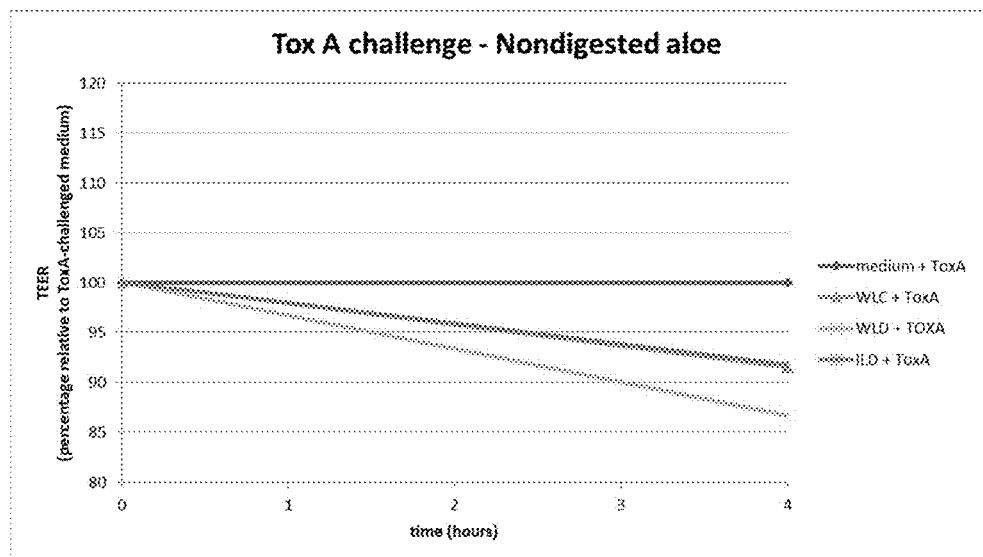
FIG. 3 shows relative change in epithelial barrier strength as compared with the medium and a digested control sample for samples WLC (5×), WLD (100×), and ILD (200×), treated with *Clostridium* toxin (ToxA).
Figure 4:
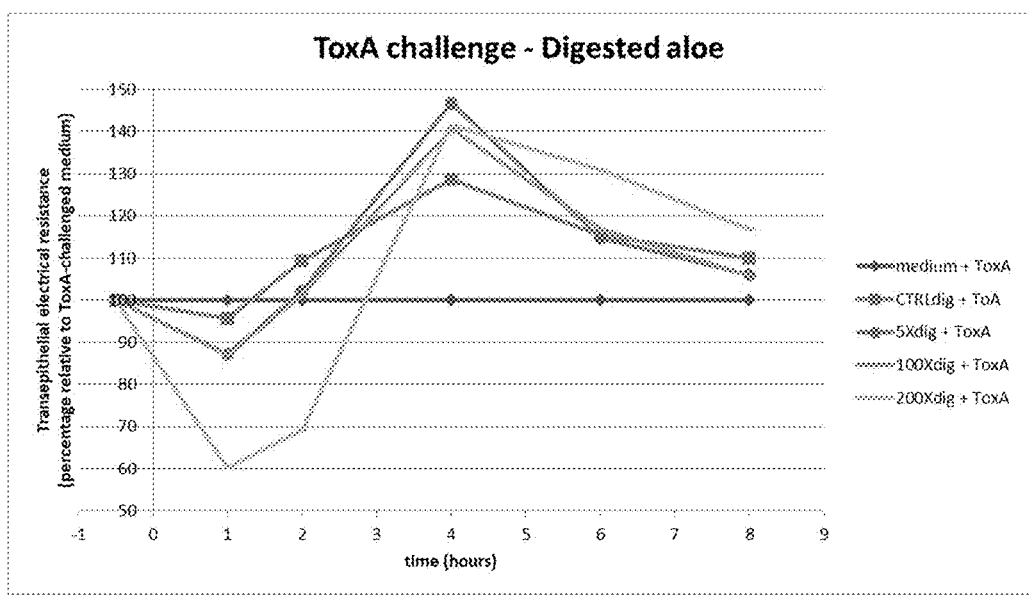
FIG. 4 shows relative change in epithelial barrier strength as compared with a digested control sample for digested samples WLC (5×), WLD (100×), and ILD (200×), treated with *Clostridium* toxin (ToxA).

Tox A gradually reduces barrier integrity. After treating the Caco-2 cells with toxin, the cells were separately treated with digested or non-digested samples of WLC, WLD, and ILD. As shown in FIG. 3, the cells treated with non-digested extracts for 4 hours did not result in an increase in TEER. On the other hand, cells treated with digested WLC and WLD increased TEER at 4 hours (p<0.001 in both cases). ILD also showed non-significant (P=0.056) increased TEER compared with control (FIG. 4).

Figure 5:
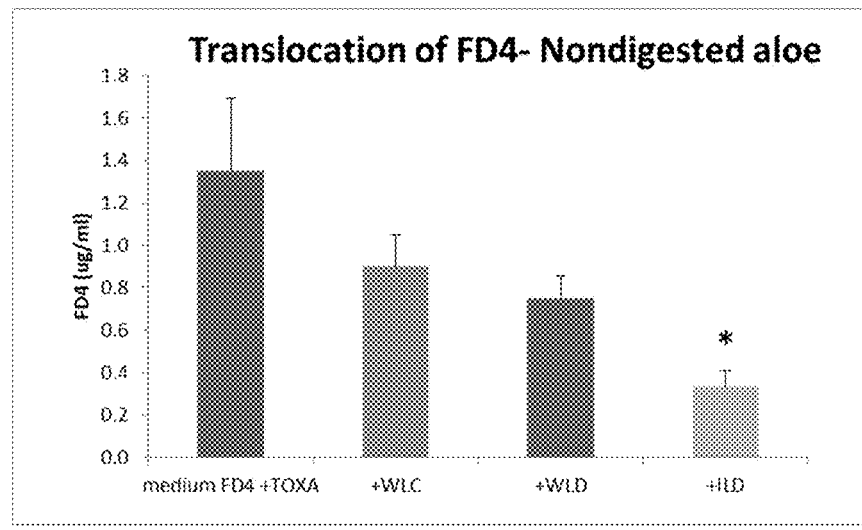
FIG. 5 shows the effect on translocation of FD4 across an epithelial barrier for selected samples WLC (5×), WLD (100×), and ILD (200×), in the presence of *Clostridium* toxin (ToxA).
Figure 6:
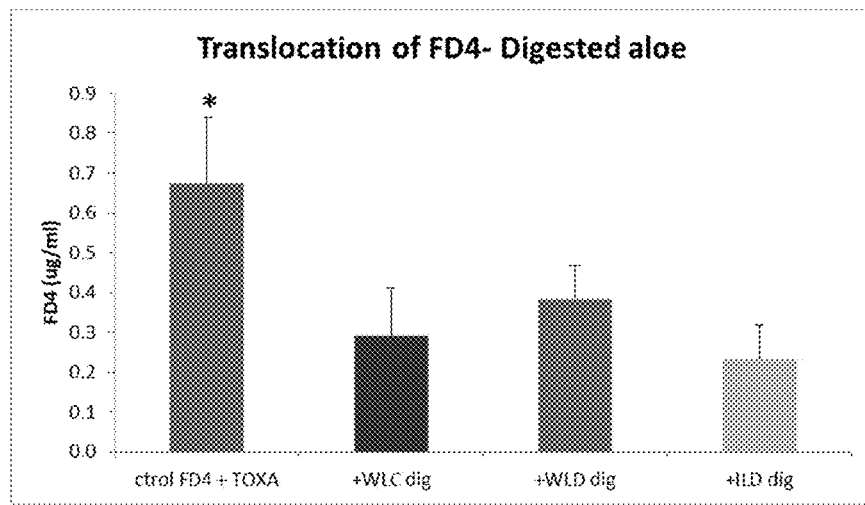
FIG. 6 shows the effect on translocation of FD4 across an epithelial barrier for selected digested samples WLC (5×), WLD (100×), and ILD (200×), in the presence of *Clostridium* toxin (ToxA).

The paracellular barrier integrity was also measured by investigating the transfer of FD4. In contrast to TEER measurements, after four hour of treatment with non-digested ILD (200×), FD4 translocation from the apical to the basolateral side was lowered (p<0.001) (FIG. 5). As shown in FIG. 6, after 4 hours of treatment, all three digested samples [WLC (5×dig), WLD (100×dig), and ILD (200× dig)] showed a decrease in FD4 translocation (p<0.01 in all cases). This indicated that despite a degrading barrier integrity as measured with TEER, these samples reduced the transfer of FD4 from the apical (luminal) to the basolateral (serosal) side.

Example 4. Effect on Caco-2 Gene Transcription

Transcription profiling was performed to better understand the improved barrier function of cells treated with decolorized aloe samples. Transcriptional changes to the Caco-2 cell line were induced by exposing the cells to the different decolorized samples of *Aloe vera* extracts for 24 hours. Gene transcription was analyzed using microarray (Affymetrix human gene 1.1 ST array).

Concerning improved barrier function by the aloe extracts, differential expression of genes related to tight junction formation and regulation and to growth factors were characterized. A subset of the claudin family genes (Claudin-1/9/10/15) were downregulated in Caco-2 cells treated by each non-digested aloe extract whereas claudin-14 was upregulated. Interestingly, MarvelD3, a tight junction-associated transmembrane protein of the occludin family, was upregulated by non-digested ILD, whereas MarvelD2 was downregulated by WLC and ILD. On the other hand, Claudin-6/15/18 and occludin, the main component of the tight junctions together with the claudin group of proteins, was downregulated by digested aloe extract, whereas Claudin-23 was upregulated by digested WLD and ILD, and MarvelD3 was upregulated by WLC and ILD, respectively.

An alternative mechanism to explain the enhanced TEER values and the reduced FD4 passage can be enhanced wound healing. Especially in the setting where Caco-2 cells were challenged, enhanced growth of cells would also increase the barrier strength. Analysis of gene transcription of growth factors revealed a limited amount of significantly affected genes for the non-digested samples and for the digested samples. Among the non-digested extracts, WLC and ILD upregulated Fibroblast growth factor-22 (FGF22) while WLD upregulated Platelet-derived growth factor D (PDGFD). Among the digested extracts, WLC and ILD upregulated Insulin-like growth factor-1 (IGF1). WLD upregulated FGF10.

Among the genes coding for cytokines and chemokines, CCL3 and CCL13 were downregulated in Caco-2 cells treated with by each decolorized non-digested aloe extract while IL-2 was downregulated by each digested extract. Genes upregulated by non-digested WLC included CXCL10, IFNA13, and IFNA5 while IL1A, IL32, CCL7, TNFSF11, TNFAIP8, CCL13, IL18, XCL1, while CCL3 were downregulated. In contrast, digested WLC upregulated CCL8 and CXCL9 while downregulating IL17F, CCL18, IL2, and IL20. Non-digested WLD upregulated CCL3L3, TNFSF13, and ENE while downregulating IFNL3, CXCL9, CCL15, TNFSF11, TNFAIP8, CCL13, IL18, XCL1, CCL27, and CCL3. In contrast, digested WLD upregulated IFNL3 and IFNA1 while downregulating IL2, IFNG, IL20, and CXCL8. Non-digested ILD upregulated CCL4L2, IFNA1, TNFSF18, IFNL1, CCL11, Th1F10, and IL1B while downregulating CCL13, IL18, IL37, CCL27, and CCL3. In contrast, digested ILD upregulated IL37 and IL12B while downregulating TNFSF18, IFNA5, and IL2.

The polarization of macrophages to either M1 (inflammatory) or M2 (anti-inflammatory) reflects the extremes of macrophage plasticity which is reflected in the amount of significantly affected genes. Human primary macrophages stimulated by each of the decolorized aloe samples (WLC, WLD, and ILD) most strongly produced CXCL8 (M1), CXCL5 (M1), CCL24 (M2), CCL4 (M1 and M2), and IL-6. Pathway analysis revealed macrophages activation which appeared to involve both M1 and M2 polarization, while macrophages stimulated by WLC and ILD showed significantly reduced phagocytosis (M1), compared to non-stimulated macrophages. The results indicated that the decolorized *Aloe vera* samples possessed a signature immunomodulatory potential that could attract a broad range of immune cells.

Taken together, the results of transcriptional profiling suggest that each decolorized sample of non-digested and digested aloe extracts tested possess both common and unique biological activity concerning tight junction assembly, epithelial barrier function, and immune modulation.

What is claimed is:

1. A method for repairing wound injury to the epithelial cell barrier between the inside of the small intestines and the rest of the body of a human in need thereof consisting essentially of:
    identifying a human in need of repairing wound injury to the epithelial cell barrier between the inside of the small intestine and the rest of the body of the human in need thereof; and
    administering to the human in need thereof a decolorized *Aloe vera* extract, wherein the *Aloe vera* extract is selected from the group consisting of whole leaf *Aloe vera* extract, whole leaf dry *Aloe vera* extract, inner leaf dry *Aloe vera* extract, digested whole leaf *Aloe vera* extract, digested whole leaf dry *Aloe vera* extract, digested inner leaf dry *Aloe vera* extract, or a combination thereof, wherein the *Aloe Vera* extract is administered at a concentration of about 0.5 mg/ml to about 2 mg/ml to the human in need thereof to effectively repair the wound injury to the epithelial cell barrier between the inside of the small intestines and the rest of the body of the human in need thereof.

2. The method of claim 1, wherein the *Aloe vera* extract is administered at a concentration of about 1 mg/ml.

3. The method of claim 1, wherein the *Aloe vera* extract is a whole leaf extract.

4. The method of claim 1, wherein the *Aloe vera* extract is a whole leaf dry extract.

5. The method of claim 1, wherein the *Aloe vera* extract is an inner leaf dry extract.

6. The method of claim 1, wherein the *Aloe vera* extract is a digested whole leaf extract.

7. The method of claim 1, wherein the *Aloe vera* extract is a digested whole leaf dry extract.

8. The method of claim 1, wherein the *Aloe vera* extract is a digested inner leaf dry extract.

\* \* \* \* \*